US005773628A

United States Patent [19]
Akhavan-Tafti et al.

[11] Patent Number: 5,773,628
[45] Date of Patent: Jun. 30, 1998

[54] 1,2-DIOXETANE COMPOUNDS WITH HALOALKOXY GROUPS, METHODS PREPARATION AND USE

[75] Inventors: Hashem Akhavan-Tafti; Zahra Arghavani, both of Sterling Heights; Robert A. Eickholt; Khaledur S. Rashid, both of Troy, all of Mich.

[73] Assignee: Tropix, Inc., Bedford, Mass.

[21] Appl. No.: 339,085

[22] Filed: Nov. 14, 1994

[51] Int. Cl.$^6$ .......................... C07D 321/00; C09K 3/00; C07C 43/176; C12Q 1/25
[52] U.S. Cl. .......................... 549/221; 549/332; 252/700
[58] Field of Search .............................. 549/332; 252/700

[56] References Cited

U.S. PATENT DOCUMENTS

| | | | |
|---|---|---|---|
| 4,857,652 | 8/1989 | Schaap | 549/510 |
| 4,931,223 | 6/1990 | Bronstein et al. | 252/700 |
| 4,952,707 | 8/1990 | Edwards | 549/221 |
| 4,956,477 | 9/1990 | Bronstein et al. | 549/221 |
| 4,959,182 | 9/1990 | Schapp | 252/700 |
| 4,962,182 | 10/1990 | Schaap | 536/18.1 |
| 4,983,779 | 1/1991 | Schaap | 568/660 |
| 5,004,565 | 4/1991 | Schapp | 252/700 |
| 5,068,339 | 11/1991 | Schapp et al. | 548/110 |
| 5,112,960 | 5/1992 | Bronstein | 536/18.1 |
| 5,132,204 | 7/1992 | Urdea | 435/4 |
| 5,145,772 | 9/1992 | Voyta et al. | 435/4 |
| 5,220,005 | 6/1993 | Bronstein | 536/26.21 |
| 5,225,584 | 7/1993 | Brooks et al. | 558/189 |
| 5,248,618 | 9/1993 | Haces | 436/172 |
| 5,326,882 | 7/1994 | Bronstein | 549/16 |
| 5,451,347 | 9/1995 | Akhavan-Tafti et al. | 252/700 |

FOREIGN PATENT DOCUMENTS

| | | |
|---|---|---|
| 0 473 984 | 3/1992 | European Pat. Off. . |
| 561033 | 9/1993 | European Pat. Off. . |
| 8800695 | 1/1988 | WIPO . |

OTHER PUBLICATIONS

A. P. Schaap and S. Gagnon, J. Amer. Chem. Soc., 104, 3504 (1982).
T. Wilson, Int. Rev. Sci.: Chem., Ser. Two, 9, 265 (1976).
T. Wilson, et al, Amer. Chem. Soc., 95, 4765 (1973).
P. D. Bartlett, et al., J. Amer. Chem. Soc., 96, 5557, (1974).
A.P. Schaap, et al., Tetrahedron Lett., 1155 (1987).
W. Adam., et al., Tetrahedron, 49(11), 2227–38 (1993).
W. Adam, et al., Chem. Ber., 125, 2455–61 (1992).
A. P. Schaap, et al., Tetrahedron Lett., 935 (1987).
A. P. Schaap, et al., Tetrahedron Lett., 1159 (1987).
A. P. Schaap, Photochem. Photobiol. 47S 50S (1988).
M. Ryan, et al., Anal. Biochem., 214(2) 548–56 (1993).
A. P. Schaap, et al., Clin. Chem., 35(9), 1863 (1989).

*Primary Examiner*—Mukund J. Shah
*Assistant Examiner*—King Lit Wong
*Attorney, Agent, or Firm*—Oblon, Spivak, McClelland, Maier & Neustadt, P.C.

[57] ABSTRACT

A chemiluminescent assay method and compositions are described which use a haloalkoxy group-substituted dioxetane which is deprotected by a hydrolytic enzyme to undergo a chemiluminescent reaction. Chemiluminescent 1,2-dioxetane compounds substituted on the dioxetane ring with a haloalkoxy group which can be triggered by a reagent to generate light are disclosed. Haloalkoxy group-substituted dioxetanes are useful for the detection of triggering agents including enzymes. The enzyme may be present alone or linked to a member of a specific binding pair in an immunoassay, DNA probe assay or other assay where the enzyme is bound to a reporter molecule.

5 Claims, 6 Drawing Sheets

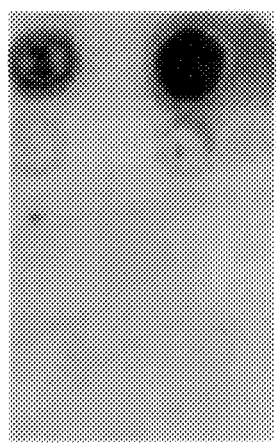 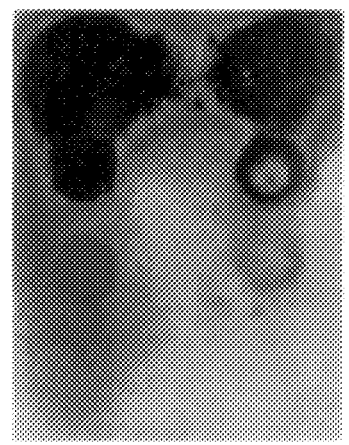
amol of AP
1120
112
11.2
1.12
Dioxetane 2     Dioxetane 5
FIG.6

1,2-DIOXETANE COMPOUNDS WITH HALOALKOXY GROUPS, METHODS PREPARATION AND USE

BACKGROUND OF THE INVENTION

(1) Field of the Invention

The present invention relates to chemiluminescent 1,2-dioxetane compounds which can be triggered by chemical reagents, including enzymes, to generate light. In particular, the present invention relates to stable aryl group-substituted 1,2-dioxetanes further substituted on the dioxetane ring with a haloalkoxy group, wherein the stable 1,2-dioxetane forms an unstable dioxetane compound by removal of a protecting group and wherein the unstable dioxetane compound decomposes to produce light and two carbonyl compounds.

(2) Description of Related Art a. Chemically Triggerable Dioxetanes

The first example in the literature is described in relation to the hydroxy-substituted dioxetane derived from the 2,3-diaryl-1,4-dioxene (A. P. Schaap and S. Gagnon, *J. Amer. Chem. Soc.*, 104, 3504 (1982)). However, the hydroxy-substituted dioxetane and any other examples of the dioxetanes derived from the diaryl-1,4-dioxenes are relatively unstable having half-lives at 25° C. of only a few hours. Further, these non-stabilized dioxetanes are destroyed by small quantities of amines (T. Wilson, *Int. Rev. Sci.: Chem., Ser. Two*, 9, 265 (1976)) and metal ions (T. Wilson, M. E. Landis, A. L. Baumstark, and P. D. Bartlett, *J. Amer. Chem. Soc.*, 95, 4765 (1973); P. D. Bartlett, A. L. Baumstark, and M. E. Landis, *J. Amer. Chem. Soc.*, 96, 5557 (1974)), both components used in the aqueous buffers for biological assays.

Examples of the chemical triggering of adamantyl-stabilized dioxetanes were first reported in U.S. patent application (A. P. Schaap, patent application Ser. No. 887, 139, filed Jul., 17, 1986) and a paper (A. P. Schaap, T. S. Chen, R. S. Handley, R. DeSilva, and B. P. Giri, *Tetrahedron Lett.*, 1155 (1987)). These dioxetanes exhibit thermal half-lives of years but can be triggered to produce efficient chemiluminescence on demand. Benzofuranyl dioxetanes substituted with trialkylsilyl and acetyl-protected phenolic groups which produce weak chemiluminescence have also been reported (W. Adam, R. Fell, M. H. Schulz, *Tetrahedron*, 49(11), 2227–38 (1993); W. Adam, M. H. Schulz, *Chem. Ber.*, 125, 2455–61 (1992)).

b. Enzymatically Triggerable Dioxetanes

Dioxetanes which can be triggered by an enzyme to undergo chemiluminescent decomposition are disclosed in U.S. patent application (A. P. Schaap, patent application Ser. No. 887,139) and a series of papers (A. P. Schaap, R. S. Handley, and B. P. Giri, *Tetrahedron Lett.*, 935 (1987); A. P. Schaap, M. D. Sandison, and R. S. Handley, *Tetrahedron Lett.*, 1159 (1987) and A. P. Schaap, *Photochem. Photobiol.*, 47S, 50S (1988)). The highly stable adamantyl-substituted dioxetanes bearing a protected aryloxide substituent are triggered to decompose with emission of light by the action of an enzyme in an aqueous buffer to give a strongly electron-donating aryloxide anion which dramatically increases the rate of decomposition of the dioxetane. As a result, chemiluminescence is emitted at intensities several orders of magnitude above that resulting from slow thermal decomposition of the protected form of the dioxetane. U.S. Pat. No. 5,068,339 to Schaap discloses enzymatically triggerable dioxetanes with covalently linked fluorescer groups. Decomposition of these dioxetanes results in enhanced and red-shifted chemiluminescence through intramolecular energy transfer to the fluorescer. U.S. Pat. No. 4,952,707 to Edwards discloses enzymatically triggerable dioxetanes bearing an adamantyl group and 2,5- or 2,7-disubstituted naphthyl groups. U.S. Pat. Nos. 5,112,960, 5,220,005, 5,326, 882 and a PCT application (88- 00695) to Bronstein disclose triggerable dioxetanes bearing adamantyl groups substituted with various groups including chlorine, bromine carboxyl, hydroxyl, methoxy and methylene groups. A publication (M. Ryan, J. C. Huang, O. H. Griffith, J. F. Keana, J. J. Volwerk, *Anal. Biochem.*, 214(2), 548–56 (1993)) discloses a phosphodiester-substituted dioxetane which is triggered by the enzyme phospholipase. U.S. Pat. No. 5,132,204 to Urdea discloses dioxetanes which require two different enzymes to sequentially remove two linked protecting groups in order to trigger the chemiluminescent decomposition. U.S. Pat. No. 5,248,618 to Haces discloses dioxetanes which are enzymatically or chemically triggered to unmask a first protecting group generating an intermediate which spontaneously undergoes an intramolecular reaction to split off a second protecting group in order to trigger the chemiluminescent decomposition.

c. Enhanced Chemiluminescence from Dioxetanes in the Presence of Surfactants

Enhancement of chemiluminescence from the enzyme-triggered decomposition of a stable 1,2-dioxetane in the presence of water-soluble substances including an ammonium surfactant and a fluorescer has been reported (A. P. Schaap, H. Akhavan and L. J. Romano, *Clin. Chem.*, 35(9), 1863 (1989)). Fluorescent micelles consisting of cetyltrimethylammonium bromide (CTAB) and 5-(N-tetradecanoyl) aminofluorescein capture the intermediate hydroxy-substituted dioxetane and lead to a 400-fold increase in the chemiluminescence quantum yield by virtue of an efficient transfer of energy from the anionic form of the excited state ester to the fluorescein compound within the hydrophobic environment of the micelle.

U.S. Pat. Nos. 4,959,182 and 5,004,565 to Schaap describe additional examples of enhancement of chemiluminescence from chemical and enzymatic triggering of stable dioxetanes in the presence of the quaternary ammonium surfactant CTAB and fluorescers. Fluorescent micelles formed from CTAB and either the fluorescein surfactant described above or 1-hexadecyl-6-hydroxybenzothiazamide enhance chemiluminescence from the base-triggered decomposition of hydroxy- and acetoxy-substituted dioxetanes. It was also reported that CTAB itself can enhance the chemiluminescence of a phosphate-substituted dioxetane.

U.S. Pat. No. 5,145,772 to Voyta discloses enhancement of enzymatically generated chemiluminescence from 1,2-dioxetanes in the presence of polymers with pendant quaternary ammonium groups alone or admixed with fluorescein. Other substances reported to enhance chemiluminescence include globular proteins such as bovine albumin and quaternary ammonium surfactants. Other cationic polymer compounds were of modest effectiveness as chemiluminescence enhancers; nonionic polymeric compounds were generally ineffective and the only anionic polymer significantly decreased light emission. European Patent application Serial No. 92113448.2 to Akhavan-Tafti published on Sep. 22, 1993 discloses enhancement of enzymatically generated chemiluminescence from 1,2-dioxetanes in the presence of polyvinyl phosphonium salts and polyvinyl phosphonium salts to which fluorescent energy acceptors are covalently attached. Co-pending application U.S. Ser. No. 08/082,091 to Akhavan-Tafti filed Jun. 24, 1993 discloses enhancement of enzymatically generated chemiluminescence from 1,2-dioxetanes in the presence of dicationic phosphonium salts.

The enzymatically triggerable dioxetanes are now undergoing widespread use as substrates for marker enzymes in numerous applications including immunoassays, gene expression studies, western blotting, Southern blotting, DNA sequencing and the identification of nucleic acid segments in infectious agents. Despite the growing use of these compounds, there still exists the need for further improving the properties of triggerable dioxetanes for use in assay methods. Triggerable dioxetanes which reach maximum light intensity more rapidly on triggering are desirable. The present invention seeks to provide such dioxetanes.

OBJECTS

It is an object of the present invention to provide novel stable aryl group-substituted 1,2-dioxetanes further substituted on the dioxetane ring with a haloalkoxy group which are thermally and hydrolytically stable at room temperature over an extended period of time. It is also an object of the present invention to provide stable aryl group-substituted 1,2-dioxetanes further substituted on the dioxetane ring with a haloalkoxy group which can be triggered to decompose with the generation of chemiluminescence. It is an object of the present invention to provide a method and compositions containing a stable aryl group-substituted 1,2-dioxetane further substituted on the dioxetane ring with a haloalkoxy group which can be triggered by chemical reagents, including enzymes, to generate chemiluminescence. Further, it is an object of the present invention to provide a method and compositions for enhancing the chemiluminescence by providing a substance which provides a hydrophobic environment in which the light emitting reaction can occur. It is a further object of the present invention to provide a method and compositions for enhancing the chemiluminescence through energy transfer to a fluorescent compound maintained in close proximity with the dioxetane. Dioxetane compounds of the present invention have superior light-generating ability and provide significant advantages when used for the detection of enzymes, and for use in immunoassays and the detection of enzyme-linked nucleic acids, antibodies, haptens and antigens by generally known methods.

IN THE DRAWINGS

FIG. 1 is a graph showing the time profiles of the chemiluminescence intensity emitted by 100 μL of a reagent containing dioxetane 5 (4-(2,2,2-trifluoroethoxy)-4-(3-phosphoryloxyphenyl)spiro[1,2-dioxetane-3,2'-tricyclo-[3.3.1.1$^{3,7}$]decane] disodium salt) and various amounts of an enhancer triggered at 37° C. by addition of $1.12 \times 10^{-17}$ mol of alkaline phosphatase (AP). The reagent consists of a 0.33 mM solution of the dioxetane 5 in 0.2M 2-amino-2-methyl-1-propanol buffer, pH 9.6 containing 0.1, 0.25, 0.5 or 1 mg/mL of 1-(tri-n-octylphosphoniummethyl)-4-(tri-n-butyl-phosphoniummethyl)benzene dichloride (Enhancer A).

FIG. 2 is a graph showing a comparison of the time profile of the chemiluminescence intensity emitted by 100 μL of a reagent containing dioxetane 5 and various amounts of an enhancer triggered at 37° C. by addition of $1.12 \times 10^{-17}$ mol of AP. The reagents consist of a 0.33 mM solution of dioxetane 5 in 0.2M 2-amino-2-methyl-1-propanol buffer, pH 9.6 containing 0.01, 0.025, 0.1 or 0.5 mg/mL of poly-vinylbenzyltributylphosphonium chloride co-polyvinylbenzyltri-octylphosphonium chloride (containing a 3:1 ratio of tributyl:trioctyl groups), Enhancer B, the preparation of which is described in European Patent Application 561,033 published Sep. 22, 1993.

FIG. 3 is a graph showing a comparison of the time profile of the chemiluminescence intensity emitted by 100 μL of enhanced reagents containing either dioxetane 2 (LUMIGEN PPD, Lumigen, Inc., Southfield, Mich.) or 5 triggered at 37° C. by addition of $1.12 \times 10^{-17}$ mol of AP. The reagents consist of 1) a 0.33 mM solution of dioxetane 2 in 0.2M 2-amino-2-methyl-1-propanol buffer, pH 9.6 containing 1.0 mg/mL of the enhancer 1-(tri-n-octylphosphoniummethyl)-4-(tri-n-butylphosphoniummethyl) benzene dichloride, and 2) a 0.33 mM solution of dioxetane 5 in 0.2M 2-amino-2-methyl-1-propanol buffer, pH 9.6 containing 0.1 mg/mL of the same enhancer. Use of dioxetane 5 of the present invention advantageously affords not only more intense chemiluminescence under these conditions but also a shorter delay until the maximum intensity is reached compared to dioxetane 2.

FIG. 4 is a graph showing a comparison of the time profile of the chemiluminescence intensity emitted by 100 μL of another pair of enhanced reagents containing either dioxetane 2 or 5 triggered at 37° C. by addition of $1.12 \times 10^{-17}$ mol of AP. The reagents consist of 1) a 0.33 mM solution of dioxetane 2 in 0.2M 2-amino-2-methyl-1-propanol buffer, pH 9.6 containing 0.5 mg/mL of Enhancer B and 2) a 0.33 mM solution of dioxetane 5 in 0.2M 2-amino-2-methyl-1-propanol buffer, pH 9.6 containing 0.25 mg/mL of the same enhancer. Use of dioxetane 5 of the present invention achieves a higher light intensity within the first 15 min which is advantageous in assays.

FIG. 5 is a graph relating the maximum chemiluminescence intensity emitted by 100 μL of a reagent containing dioxetane 5 triggered at 37° C. to the amount of AP. Chemiluminescence emission was initiated at 37° C. by addition of 3 μL of solutions of AP containing between $3.36 \times 10^{-16}$ mol and $3.36 \times 10^{-21}$ of enzyme to 100 μL of a 0.33 mM solution of dioxetane 5 in 2-amino-2-methyl-1-propanol buffer, 0.2M (pH 9.6) containing 1-(tri-n-octylphosphoniummethyl)-4-(tri-n-butyl-phosphoniummethyl)benzene dichloride, 1.0 mg/mL. The term S-B refers to the chemiluminescence signal (S) in Relative Light Units (RLU) in the presence of AP corrected for background chemiluminescence (B) in the absence of AP. The graph shows the linear detection of alkaline phosphatase. The calculated detection limit (twice the standard deviation of the background) was determined to be $1.4 \times 10^{-21}$ mol or less than 1000 molecules of alkaline phosphatase under these conditions.

FIG. 6 is a digitally scanned image of an X-ray film from an experiment detecting alkaline phosphatase on a membrane with chemiluminescence. Solutions of alkaline phosphatase in water containing from $1.1 \times 10^{-15}$ to $1.1 \times 10^{-18}$ mol were applied to identical nylon membranes (Micron Separations Inc., Westboro, Mass). The membranes were air dried for 5 min and soaked briefly with a reagent containing 1 mg/mL of Enhancer A in 0.2M 2-amino-2-methyl-1-propanol buffer, pH 9.6 containing 0.88 mM MgCl and either 0.33 mM dioxetane 2 or 0.33 mM dioxetane 5. The membranes were placed between transparent plastic sheets and exposed to X-ray film (Kodak X-OMAT AR, Rochester, N.Y.). In a comparison of the two reagents, the light produced using dioxetane 5 of the present invention led to more intense images and better detection sensitivity.

DESCRIPTION OF THE PREFERRED EMBODIMENTS

Figure 1:
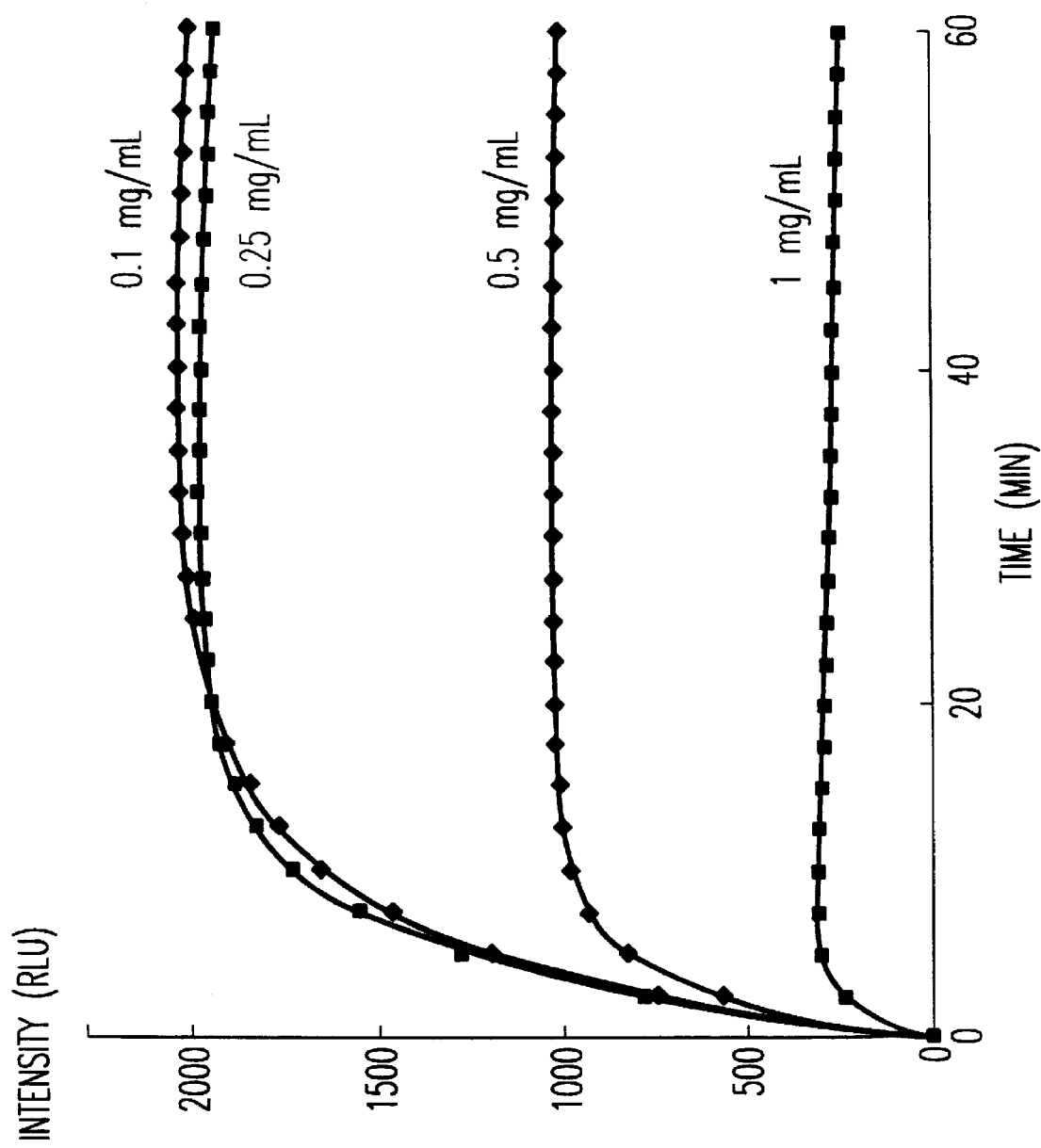

The present invention relates to stable 1,2-dioxetanes which can be triggered by chemical reagents, including enzymes, to generate chemiluminescence. Stable dioxetanes useful in practicing the present invention may be of the formula:

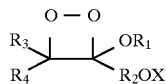

wherein $R_1$ is a haloalkyl group containing 1 to 8 carbon atoms further containing at least one halogen selected from fluorine, chlorine, bromine and iodine, wherein $R_3$ and $R_4$ are each organic groups which can be substituted or unsubstituted with heteroatoms and which provide stability to the dioxetane, wherein $R_2$ is selected from aryl, biaryl, heteroaryl, fused ring polycyclic aryl and fused ring polycyclic heteroaryl groups which can include additional substituents and wherein X is a protecting group which can be removed by a reagent selected from the group consisting of enzymes and other chemicals to form an unstable oxide intermediate dioxetane compound which decomposes and releases electronic energy to form light and two carbonyl-containing compounds as shown in Scheme 1 below.

Scheme 1

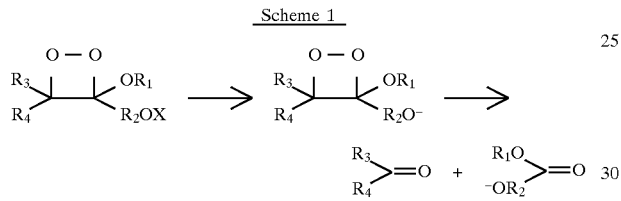

+ Light

In one embodiment, the groups $R_3$ and $R_4$ are combined together in a cyclic or polycyclic organic group $R_5$ which is spiro-fused to the dioxetane ring, containing 6 to 30 carbon atoms and which can include additional substituents and which provides thermal stability.

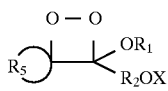

The group $R_5$ is more preferably a polycyclic group preferably an adamantyl group or a substituted adamantyl group having one or more substituent groups $R_6$ selected from halogens, alkyl, substituted alkyl, alkoxy, substituted alkoxy, carbonyl, carboxyl, phenyl, substituted phenyl, amino and alkylamino groups covalently bonded thereto.

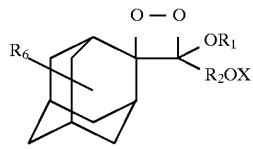

In another preferred embodiment the group $R_2$ is a phenyl or naphthyl group. It is especially preferred that $R_2$ is a phenyl group in which the OX group is oriented meta to the dioxetane ring group as shown below. The phenyl ring may contain additional ring substituents $R_7$ independently selected from halogens, alkyl, substituted alkyl, alkoxy, substituted alkoxy, carbonyl, carboxyl, amino and alkylamino groups. Some exemplary structures include, for example

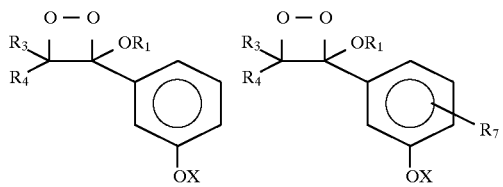

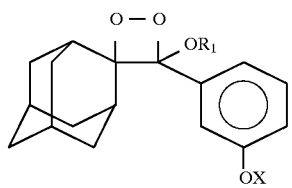

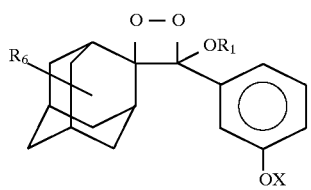

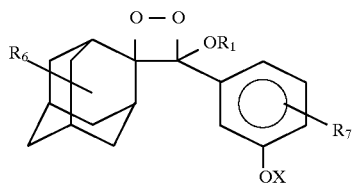

In another preferred embodiment, the group $R_1$ is a mono-, di- or polyhaloalkyl group containing one or more fluorine or chlorine atoms. It is especially preferred that the halogen atoms be located in the alkyl group such that the halogen atom or atoms are separated from the oxygen atom of the haloalkoxy group by not more than two carbon atoms.

A preferred class of dioxetane compounds is exemplified by

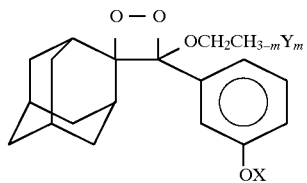

wherein Y is a halogen selected from fluorine and chlorine atoms, m is an integer between 1 and 3 and X is a group removable by chemical reagents including enzymes to form an aryloxide-substituted dioxetane.

The OX group may be selected from hydroxyl, $OOCR_8$ wherein $R_8$ is an alkyl or aryl group containing 2 to 20 carbon atoms either of which may contain heteroatoms, trialkylsilyloxy, triarylsilyloxy, aryldialkylsilyloxy, $OPO_3^{-2}$ salt, $OSO_3^-$ salt, β-D-galactosidoxy and β-D-glucuronidyloxy groups.

The stable 1,2-dioxetane compounds of the present invention have long half-lives at room temperature, typically ≧1 year, but can be triggered by a reagent to decompose rapidly with half-lives ranging from seconds to a few minutes depending on the microenvironment in which the dioxetane is located. Stable aryl group-substituted 1,2-dioxetanes further substituted on the dioxetane ring with a haloalkoxy group provide unexpected properties when triggered to remove the protecting group X to form an unstable oxide intermediate dioxetane compound which decomposes and releases electronic energy to form light and two carbonyl-containing compounds. Dioxetane compounds of the present invention undergo a more rapid chemiluminescent decomposition upon triggering than prior art compounds yet maintain a high degree of thermal and hydrolytic stability in the protected state. This combination of properties confers advantages in assay applications using enzymatically triggered dioxetanes. The rapid chemiluminescent decomposition allows the light to be produced more quickly leading to decreased assay times. Higher light intensities in blotting applications also result from the more rapid onset of chemiluminescence. No existing theory of dioxetane chemiluminescence adequately accounts for or predicts the rapid chemiluminescence kinetics of dioxetanes of the present invention.

The present invention further relates to compositions containing a haloalkyl-substituted 1,2-dioxetane which can be triggered by a reagent, including enzymes and other chemicals, to generate chemiluminescence in the presence of an enhancer substance. Enhancers are substances which increase the quantity of light produced by triggering the chemiluminescent reaction above the amount which is produced in the absence of the enhancer. Enhancers suitable for use in practicing the present invention and which are incorporated herein by reference include: (1) quaternary ammonium salt surfactants which form micelles in aqueous solution alone or admixed with a fluorescent cosurfactant as described in U.S. Pat. Nos. 4,959,182 and 5,004,565 to Schaap; (2) polymeric quaternary ammonium salt surfactants as described in U.S. Pat. No. 5,145,772 to Voyta; (3) polymeric phosphonium salt surfactants especially polyvinylbenzyltrialkylphosphonium-containing homopolymers and copolymers as described in European Patent application Serial No. 92113448.2 to Akhavan-Tafti published on Sep. 22, 1993; (4) dicationic phosphonium or ammonium salt surfactants of the formula:

wherein A may be P or N atoms and wherein Link is an organic spacer group containing two or more carbon atoms selected from the group consisting of substituted and unsubstituted aryl, alkyl, alkenyl, alkynyl and wherein Link may contain heteroatoms and wherein R is selected from lower alkyl or aralkyl containing 1 to 20 carbon atoms and wherein B is halide anion as described in patent application U.S. Ser. No. 08/082,091 filed Jul. 24, 1993. Compositions containing haloalkyl-substituted 1,2-dioxetanes, an enhancer as described above and additionally a fluorescent energy acceptor are also within the scope of the present invention. The degree of enhancement is dependent on the concentration of enhancer used. Amplification of the chemiluminescence intensity occurs with enhancer concentrations ranging between about 0.001% and about 10%. Enhancers are preferably used at concentrations between about 0.01% and about 0.5%. It has been found that the combination of certain phosphate-protected haloalkoxy-substituted 1,2-dioxetanes with certain enhancers when reacted with a phosphatase enzyme provide an effective reagent for producing light rapidly and with high efficiency. The unexpected advantage of these combinations in terms of speed in reaching maximum light intensity and light-generating efficiency does not parallel the behavior of other art-known dioxetane-enhancer systems. These advantages will become more apparent by consideration of the detailed examples.

The present invention relates to a method for generating light which comprises providing a stable 1,2-dioxetane of the formula:

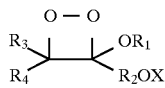

wherein $R_1$ is a haloalkyl group containing 1 to 8 carbon atoms further containing at least one halogen selected from fluorine, chlorine, bromine and iodine, wherein $R_3$ and $R_4$ are each organic groups which can be substituted or unsubstituted with heteroatoms and which provide stability to the dioxetane and wherein the X is a group that can be removed by a reagent selected from the group consisting of enzymes and other chemical reagents to form an unstable oxide intermediate dioxetane compound which decomposes and releases electronic energy to form light and two carbonyl-containing compounds of the formula:

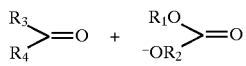

and reacting the dioxetane with the reagent to produce the light.

Further, the present invention relates to a method for producing chemiluminescence in solution or on the surface of a solid support from a stable 1,2-dioxetane triggered by a reagent selected from enzymes and other chemical agents. The present invention also relates to an improved method for detecting enzymes and other chemical agents by a chemiluminescent reaction.

When the reagent that removes the X group is an enzyme, it may be used as a conjugate to another molecule, especially as a conjugate to a member of a specific binding pair selected from haptens, antigens, antibodies, receptors, proteins, nucleic acids and oligonucleotides. Additionally the enzyme or conjugate may be deposited on a solid surface such as a bead, tube, microplate well or membrane for performing the chemiluminescent reaction. In another embodiment the reagent which removes the X group may be a chemical such as a fluoride salt, a basic salt or a nucleophilic compound in a dipolar aprotic solvent.

The present invention also relates to a method for detecting the presence or amount of a reagent which can induce the chemiluminescent decomposition of a dioxetane of the present invention in an assay wherein the reagent is selected from enzymes and other chemical agents. The invention may be used to detect the presence or quantity of an enzyme in a sample as, for example, in reporter gene assays. The invention may also be employed to advantage in an assay for a substance to be detected or quantitated by employing an enzyme conjugate of the substance to be detected or an enzyme conjugate of an analog of the substance to be detected or an enzyme conjugate of a substance which specifically binds the substance to be detected. For example, the present invention relates to a method and compositions for the detection of phosphatase enzymes, for the detection of haptens, antigens and antibodies in immunoassays, e.g. sandwich assays such as ELISA or competitive immunoassays in which a reporter enzyme may be coupled to an analyte, an analyte analog, an antibody to the analyte a member of a specific binding pair exemplified by biotin and avidin, digoxigenin and anti-digoxigenin or fluorescein and anti-fluorescein. Enzymes detectable by use of the present invention may also be used in art-recognized manners such as Western blotting for protein detection, Southern blotting, Northern blotting, DNA sequencing, DNA profiling, DNA fingerprinting and nucleic acid hybridization-based assays for the detection of enzyme-linked DNA or RNA probes. In the latter types of assays, an enzyme-labeled nucleic acid probe is hybridized with a complementary sequence of interest such as bacterial DNA or viral RNA or DNA for the detection of infectious agents or with DNA sequences associated with genetic diseases or cancer. Detection of the light emitted by the enzymatic detection reaction in an assay may be readily performed using a luminometer, X-ray film, with a camera and photographic film or with a charge-coupled device camera.

In another embodiment, dioxetanes of the invention bearing a fluorinated alkoxy group are prepared by photooxygenation of the corresponding vinyl ether precursor. Fluorinated alkoxy-substituted vinyl ethers can be prepared by reductive coupling of a ketone and a fluorinated alkyl ester by the method disclosed in U.S. Pat. Nos. 4,962,192 and 4,983,779. Surprisingly, the coupling of the latter esters under strongly reducing conditions proceeds as shown in Scheme 4 to form the expected vinyl ether despite the susceptibility of halogenated esters to reductive cleavage.

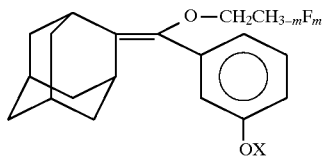

wherein m is an integer from 1 to 3, wherein the OX group may be selected from hydroxyl, $O^-M^+$ wherein M is selected from an alkali metal ion, a quaternary ammonium ion and a quaternary phosphonium ion, $OOCR_8$ wherein $R_8$ is an alkyl or aryl group containing 2 to 20 carbon atoms either of which may contain heteroatoms, trialkylsilyloxy, triarylsilyloxy, aryldialkylsilyloxy, $OPO_3^{-2}$ salt, $OSO_3^-$ salt, β-D-galactosidoxy and β-D-glucuronidyloxy groups.

In yet another embodiment, dioxetanes of the invention bearing a fluorinated alkoxy group are prepared by replacement of one OX group on a dioxetane with another OX group to form another dioxetane where the OX groups are defined above. One example of such a replacement is shown in Scheme 5 below.

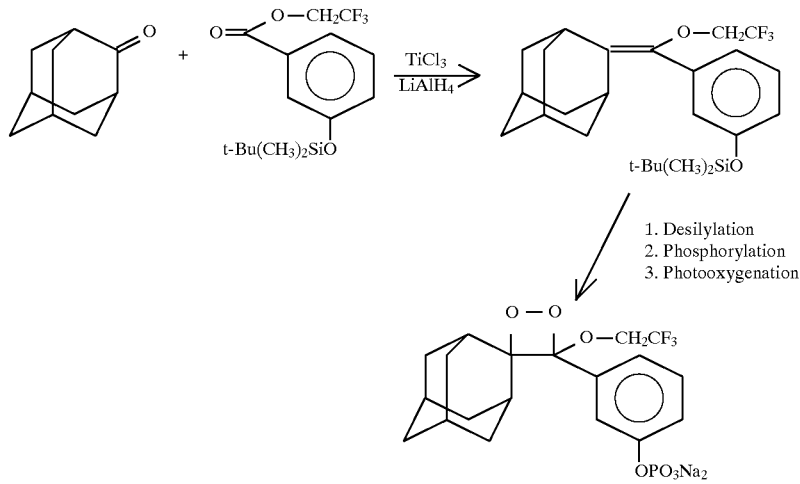

The present invention therefore further encompasses vinyl ether compounds of the formula:

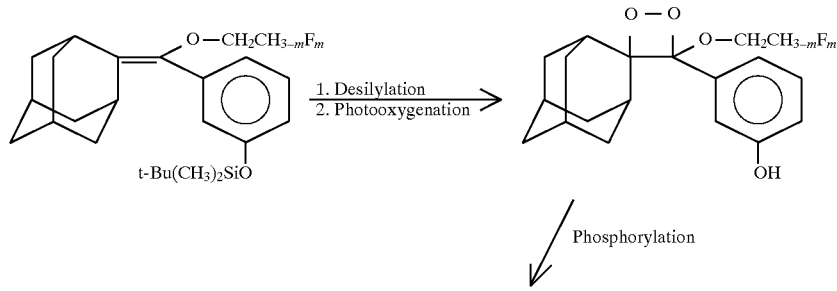

-continued
Scheme 5.

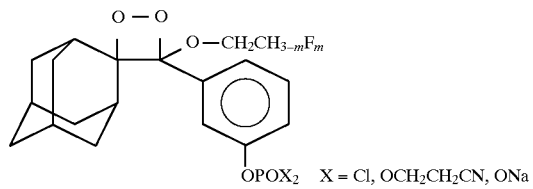

OPOX₂  X = Cl, OCH₂CH₂CN, ONa

EXAMPLES

Calf intestinal alkaline phosphatase (AP) was obtained from Biozyme (San Diego, Calif.). Other chemical reagents were obtained from Aldrich Chemical Co. (Milwaukee). Nuclear magnetic resonance (NMR) spectra were obtained on a Varian Gemini 300 spectrometer as solutions in $D_2O$ or $CDCl_3$. Chemiluminescence intensities and rate measurements were performed using either a Turner Designs (Sunnyvale, Calif.) model TD-20e luminometer, a Luminoskan luminometer (Helsinki, Finland), a charge-coupled device camera luminometer constructed in the inventors' laboratory or a luminometer constructed in the inventors' laboratory consisting of an electrically heated sample block, an optical fiber and associated optics for light collection and a photomultiplier tube. Temperature control of samples analyzed in the commercial luminometers was achieved by means of a circulating bath connected to the instrument. Quantitative measurement of light intensities on the Turner luminometer was extended beyond the $10^4$ linear range of the detector by a neutral density filter. Data collection from each of the instruments was controlled by an Apple MacIntosh SE/30 computer using the LUMISOFT data reduction program (Lumigen).

TABLE 1

Dioxetane Compounds

| Dioxetane | R | OX |
|---|---|---|
| 1 | CH₃ | OH |
| 2 | CH₃ | OPO₃Na₂ |
| 3 | CH₂CF₃ | OH |
| 4 | CH₂CF₃ | OPO(OCH₂CH₂CN)₂ |
| 5 | CH₂CF₃ | OPO₃Na₂ |
| 6 | CH₂CF₃ | OOCCH₃ |
| 7 | CH₂CHF₂ | OH |
| 8 | CH₂CH₂F | OH |
| 9 | CH₂CH₂Cl | OH |

Example 1

Synthesis of Dioxetanes 1 and 2

4-Methoxy-4-(3-hydroxyphenyl)spiro[1,2-dioxetane-3,2'-tricyclo[3.3.1.1³,⁷]-decane] 1.

[(3-Hydroxyphenyl)methoxymethylene]tricyclo[3.3.1.1³,⁷]decane (preparation described in U.S. Pat. Nos. 4,962,192 and 4,983,779) was converted to the dioxetane by the method described in U.S. Pat. No. 5,004,565. Dioxetane 2 is commercially available as LUMIGEN PPD (Lumigen, Inc., Southfield, Mich.).

Example 2

Synthesis of Dioxetane 3

(a) Synthesis of 2,2,2-trifluoroethyl 3-hydroxybenzoate. A solution of 20 g of methyl 3-hydroxybenzoate in 150 mL of trifluoroethanol containing 6 mL of $H_2SO_4$ was refluxed for 3.5 hours. Another 6 mL of $H_2SO_4$ was added and reflux continued overnight. The cooled solution was poured onto 600 g of ice and cautiously neutralized. The water was extracted with ethyl acetate (ca. 1.5 L). The ethyl acetate solution was dried and evaporated producing an oil which was purified by column chromatography with 10% ethyl acetate in hexane. Yield 19.7 g; $^1H$ NMR (CDCl₃) δ 4.65–4.73 (q,2H), 6.10 (bs,1H), 7.10–7.13 (dd,1H), 7.32–7.38 (t,1H), 7.54–7.56 (t,1H), 7.63–7.66 (dd,1H).

(b) Synthesis of 2,2,2-trifluoroethyl 3-t-butyldimethylsilyloxybenzoate. A solution of 1.82 g (1.2 eq.) of t-butyldimethylsilyl chloride and 0.82 g (1.2 eq.) of imidazole in 3 mL of DMF was stirred under argon for 15 min. The ester of part (a) (2.22 g, 10 mmol) in 7 mL of DMF was added and the resulting solution stirred overnight. The solution was poured into 125 mL of water and extracted with hexane. The hexane was dried and evaporated leaving an oil which was chromatographed on silica with 10% ethyl acetate in hexane. Yield 3.18 g; $^1H$ NMR (CDCl₃) δ 0.23 (s,6H), 1.00 (s,9H), 4.65–4.73(q,2H), 7.07–7.11 (dd,1H), 7.31–7.34 (t,1H), 7.52–7.54 (t,1H), 7.66–7.70 (dd,1H).

(c) Synthesis of [(3-t-butyldimethylsilyloxyphenyl)-(2,2,2-trifluoroethyl)methylene]tricyclo[3.3.1.1³,⁷]decane. A three neck flask was purged with argon and charged with 200 mL of anhydrous THF. The flask was cooled in an ice bath and titanium trichloride (20.25 g, 0.131 mol) was added with stirring. Lithium aluminum hydride (LAH) (2.36 g, 0.066 mol) was added in small portions causing a brief exothermic reaction. After all of the LAH was added the cooling bath was removed and triethylamine (18.3 mL, 0.131 mol) was added. The black mixture was refluxed for 100 min under argon and then cooled for 15 min. A solution of adamantanone (5.92 g, 39 mmol) and 2,2,2-trifluoroethyl 3-tert-butyldimethylsilyloxybenzoate (4.39 g, 13 mmol) in 30 mL of dry THF was added dropwise over 10 min. Reaction progress was monitored by TLC with 20% ethyl acetate in hexane. The crude reaction mixture was diluted with hexane and decanted. The residue was washed several times using a total of ca. 1 L of hexane. The combined hexane solution was filtered and evaporated leaving an oil which was purified by column chromatography on silica gel, eluting with 1.5% ethyl acetate in hexane yielding 3.5 g of alkene; $^1H$ NMR (CDCl₃) δ 0.20 (s,6H), 1.00 (s,9H), 1.60–2.05 (m,12H), 2.61 (s,1H), 3.29 (s, 1), 3.70–3.79 (q,2H), 6.78–6.83 (m,2H), 6.89–6.92 (dd,1H), 7.20–7.25 (t,1H).

(d) Synthesis of [(3-hydroxyphenyl)-(2,2,2-trifluoroethyl)-methylene]tricyclo[3.3.1.1³,⁷]decane. The silyl-protected alkene (3.5 g, 7.7 mmol) was deprotected by reaction with 2.44 g (1 eq.) of tetrabutylammonium fluoride in 40 mL of dry THF. After stirring one hour, the solution was evaporated and the residue poured into 150 mL of water. The water solution was extracted with three 150 mL portions of ethyl acetate. The combined organic solution was dried and evaporated and the residue chromatographed using 1.5–10% ethyl acetate in hexane. Residual t-butyldimethylsilanol was removed under reduced pressure at 50° C. This produced 1.25 g of the deprotected alkene; $^1$H NMR (CDCl$_3$) δ 1.78–1.98 (m,12H), 2.63 (s, 1H), 3.29 (s,1H), 3.71–3.79 (q,2H), 5.27 (s,1H), 6.79–6.82 (m,2H), 6.87–6.89 (dd,1H), 7.21–7.24 (t,1H).

(e) Synthesis of 4-(2,2,2-Trifluoroethoxy)-4-(3-hydroxyphenyl)spiro[1,2-dioxetane-3,2'-tricyclo[3.3.1.1$^{3,7}$]decane] (3). The alkene (51 mg) in 20 mL of CH$_2$Cl$_2$ was photooxygenated for 90 min at −78° C. using polymer-bound Rose Bengal. TLC showed complete consumption of the alkene and formation of a new material which emitted blue-green light when the plate was heated as well as dioxetane decomposition products. The sensitizer was filtered off, the solvent evaporated and the crude product chromatographed using 10% ethyl acetate in hexane yielding 24 mg of the dioxetane: $^1$H NMR (CDCl$_3$) δ 1.01–1.06 (m, 1H), 1.26–1.31 (m, 1H), 1.49–1.92 (m, 10H), 2.25 (br s, 1H), 3.06 (br s, 1H), 3.565–3.685 (dq, 1H), 3.870–3.992 (dq, 1H), 5.180 (s, 1H), 6.911–6.946 (dd, 1H), 7.2 (br s, 2H), 7.337 (t, 1H).

Example 3

Synthesis of Dioxetane 4

4-(2,2,2-Trifluoroethoxy)-4-(3-bis(cyanoethyl) phosphoryloxyphenyl)spiro[1,2-dioxetane-3,2'-tricyclo [3.3.1.1$^{3,7}$]decane].

(a) A solution of POCl$_3$ (1.0 mL, 3.3 eq.) in 10 mL of CH$_2$Cl$_2$ was placed under argon and cooled to 0° C. Anhydrous pyridine (2.6 mL, 10 eq.) was added and the solution stirred for 10 min to cool. A solution of dioxetane 3 (1.2 g, 1 eq.) and pyridine (2.0 mL, 8 eq.) in 10 mL of CH$_2$Cl$_2$ was added dropwise. TLC showed complete conversion of the dioxetane in 1 hour. The volatiles were removed under reduced pressure and the resulting yellow solid placed under argon.

(b) The solid from the previous step was dissolved in 15 mL of CH$_2$Cl$_2$ and 0.90 mL (4 eq.) of cyanoethanol was added followed by 3.0 mL of pyridine. After stirring overnight, the solution was concentrated and redissolved in CH$_2$Cl$_2$. Extraction with water, drying over MgSO$_4$ and evaporation left a yellow oil which was further purified by chromatography on silica with 50–100% ethyl acetate in hexane yielding the bis(cyanoethyl)phosphate dioxetane 4 as a colorless oil: $^1$H NMR (CDCl$_3$) δ 0.95 (m, 1H), 1.30 (m, 1H), 1.47–1.96 (m, 10H), 2.173 (br s, 1H), 2.819 (t, 4H), 3.051 (br s, 1H), 3.630 (dq, 1H), 3.958 (dq, 1H), 4.30–4.50 (m, 4H), 7.32–7.60 (m, 4H).

Example 4

Synthesis of Dioxetane 5 (Method 1)

4-(2,2,2-Trifluoroethoxy)-4-(3-phosphoryloxyphenyl) spiro[1,2-dioxetane-3,2'-tricyclo[3.3.1.1$^{3,7}$]decane], disodium salt.

(a) Synthesis of [(3-bis(cyanoethyl) phosphoryloxyphenyl)-(2,2,2-trifluoroethyl)methylene] tricyclo[3.3.1.1$^{3,7}$]decane. Pyridine (1.1 mL) in 3 mL of dry CH$_2$Cl$_2$ was cooled in an ice bath. POCl$_3$ (0.4 mL, 4.3 mmol) in 3.5 mL of CH$_2$Cl$_2$ was added dropwise and the solution stirred 15 min. The alkene from Example 2(d) (450 mg, 1.33 mmol) in 5 mL of CH$_2$Cl$_2$ and 0.5 mL of pyridine was added and the reaction warmed to room temperature. After 1.5 hours, TLC indicated that the reaction was incomplete so additional POCl$_3$ (0.1 mL) and pyridine (0.3 mL) were added. The reaction was judged complete after one hour. The solution was evaporated to dryness and a solution of 10 mL of CH$_2$Cl$_2$, 0.27 mL of 2-cyanoethanol (4 mmol) and 1.1 mL of pyridine was added. After 72 hours, the solution was evaporated and the residue diluted with 75 mL of CH$_2$Cl$_2$. This solution was extracted with saturated NaCl solution, dried over Na$_2$SO$_4$ and evaporated. The crude product was chromatographically purified using 50–100% ethyl acetate in hexane yielding 289 mg of product; $^1$H NMR (CDCl$_3$) δ 1.79–1.99 (m,12H), 2.61 (s,1H), 2.78–2.83 (m,4H), 3.29 (s,1H), 3.72–3.80 (q, 2H), 4.36–4.45 (m,4H), 7.17–7.23 (m,3H), 7.37–7.41 (t,1H).

(b) Synthesis of [(3-phosphoryloxyphenyl) -(2,2,2-trifluoroethoxy)methylene]tricyclo[3.3.1.1$^{3,7}$]decane, disodium salt. The bis(cyanoethyl)phosphate alkene (374 mg, 0.71 mmol) in 15 mL of acetone was stirred with a solution of 57 mg (2 eq.) of NaOH in 1 mL of water overnight. Precipitated product was collected by filtration and washed with acetone yielding 272 mg of the product. Additional NaOH (10 mg) was added to the filtrate and stirring continued for one day. A small second crop of product had precipitated and was collected; $^1$H NMR (CD$_3$OD) δ 1.79–1.98 (m,12H), 2.63 (s,1H), 3.28 (s,1H), 3.78–3.86 (q,2H),6.80–7.46 (m,4H); $^{31}$P NMR (CD$_3$OD) δ 2.60 (s).

(c) Synthesis of 4-(2,2,2-Trifluoroethoxy)-4-(3-phosphoryloxyphenyl)spiro[1,2-dioxetane-3,2'-tricyclo [3.3.1.1$^{3,7}$]-decane], disodium salt. The alkene (272 mg) in 10 mL of D$_2$O was photooxygenated using methylene blue for 90 min at 0° C. NMR showed complete conversion to the dioxetane. The dioxetane thus formed may be used directly in preparing aqueous solutions for reacting with a phosphatase enzyme.

Example 5

Synthesis of Dioxetane 5 (Method 2)

(a) The bis(cyanoethyl)phosphate dioxetane 4 (0.3367 g, 0.61 mmol) dissolved in 20 mL of methanol was stirred with 0.269 g (4.2 eq.) of sodium carbonate in 2 mL of Type I water (Lumigen) overnight. TLC showed incomplete conversion so an additional 0.1283 g of sodium carbonate in 1 mL of Type I water and 10 mL of methanol were added and stirring continued for an additional day. TLC using 30% methanol in CH$_2$Cl$_2$ showed nearly complete removal of the cyanoethyl groups. The solvents were evaporated under reduced pressure yielding a slightly yellow solid. The solid was freed of impurities by twice dissolving in methanol, filtering and evaporating the methanol. $^1$H NMR (CD$_3$OD) δ 1.16–1.36 (m, 2H), 1.52–2.10 (m, 10H), 2.34 (br s, 1H), 3.018 (br s, 1H), 3.72–3.90 (m, 2H), 7.0–7.8 (m, 4H) ; $^{31}$P NMR (CD$_3$OD) δ 2.67 (rel. to ext. H$_3$PO$_4$)

Example 6

Synthesis of Dioxetane 6

4-(2,2,2-Trifluoroethoxy)-4-(3-acetoxyphenyl)spiro[1,2-dioxetane-3,2'-tricyclo[3.3.1.1$^{3,7}$]decane]. A solution of dioxetane 3 (78.2 mg) in 15 mL of CH$_2$Cl$_2$ was placed under argon. Dry pyridine (40 μL, 2.3 eq.) was added followed after 5 min by 16.6 μL (1.1 eq.) of acetyl chloride. The reaction was judged complete by TLC after 2 hours, showing a new material which emitted blue-green light when the plate was heated. The volatiles were removed in vacuo leaving a yellow oil which was purified by preparative TLC using $CH_2Cl_2$ as eluent. A colorless oil (44 mg) was obtained: $^1H$ NMR ($CDCl_3$) δ 0.98 (m, 1H), 1.29 (m, 1H), 1.46–2.00 (m, 10H), 2.20 (br s, 1H), 2.325 (s, 3H), 3.06 (br s, 1H), 3.624 (dq, 1H), 3.938 (dq, 1H), 7.20 (dd, 1H), 7.28–7.64 (m, 3H).

Example 7

Synthesis of Dioxetane 7

4-(2,2-Difluoroethoxy)-4-(3-hydroxyphenyl)spiro[1,2-dioxetane-3,2'-tricyclo[$3.3.1.1^{3,7}$] decane].

(a) Synthesis of 2,2-difluoroethyl 3-hydroxybenzoate. A solution of 2.19 g of 3-hydroxybenzoic acid (15.9 mmol) in 4 mL of 2,2-difluoroethanol (62 mmol) containing 2 drops of $H_2SO_4$ was refluxed for 3 days. The cooled solution was poured into 75 mL of ethyl acetate. The ethyl acetate was extracted with saturated aq. $NaHCO_3$ until neutral. The ethyl acetate solution was extracted with saturated aq. NaCl, dried and evaporated under reduced pressure yielding 2.82 g of a colorless oil; $^1H$ NMR ($CDCl_3$) δ 4.51 (dt,2H, J=3.9, 13.8 Hz), 5.99 (br s, 1H), 6.073 (tt, 1H, J=3.9, 55 Hz), 7.08–7.12 (m,1H), 7.31 (t,1H), 7.54–7.55 (t,1H), 7.61–7.65 (m,1H).

(b) Synthesis of 2,2-difluoroethyl 3-t-butyldimethylsilyloxybenzoate. A solution of 2.31 g (1.1 eq.) of t-butyldimethylsilyl chloride and 1.04 g (1.1 eq.) of imidazole in 5 mL of DMF was stirred under argon for 15 min. The ester from step (a) (2.82 g, 13.9 mmol) in 5 mL of DMF was added and the resulting solution stirred overnight. The solution was diluted with 50 ML of DMF and extracted with hexane (10×75 mL) and the combined hexane solution was washed with water (2×200 ml). The hexane was dried and evaporated leaving 3.58 g of silylated ester; $^1H$ NMR ($CDCl_3$) δ 0.223 (s,6H), 1.00 (s,9H), 4.50 (dt,2H, J=3.9, 13.8 Hz), 6.083 (tt,1H, J=3.9, 55 Hz), 7.05–7.09 (m,1H), 7.322 (t,1H), 7.50–7.52 (t,1H), 7.65–7.68 (m,1H).

(c) Synthesis of [(3-t-butyldimethylsilyloxyphenyl)-(2,2-difluoroethoxy)methylene]tricyclo[$3.3.1.1^{3,7}$]decane. A three neck flask was purged with argon and charged with 60 mL of anhydrous THF. Titanium trichloride (12.19 g, 79 mmol) was added with stirring and the flask was cooled in an ice bath. Lithium aluminum hydride (1.42 g, 39.5 mmol) was added in small portions causing a brief exothermic reaction. After all of the LAH was added the cooling bath was removed and triethylamine (11 mL, 79 mmol) was added. The black mixture was refluxed for 140 min under argon and then heating stopped. A solution of adamantanone (3.56 g, 23.7 mmol) and 2,2-difluoroethyl 3-t-butyldimethylsilyloxybenzoate (2.50 g, 7.9 mmol) in 10 mL of dry THF was added dropwise over 5 min. Reaction progress was monitored by TLC with 25% ethyl acetate in hexane. After 20 min, the mixture was diluted with hexane and decanted. The residue was washed with hexane (7×100 mL) and the combined hexane solution was filtered and evaporated leaving an oil which was purified by column chromatography on silica gel, eluting with 5% ethyl acetate in hexane. A fraction was collected containing 3.1 g of a mixture of the alkene and adamantylideneadamantane. The mixture was carried on to the next step.

(d) Synthesis of [(2,2-difluoroethoxy)-(3-hydroxyphenyl)methylene]tricyclo[$3.3.1.1^{3,7}$]decane. The impure silyl-protected alkene (3.1 g) was deprotected by reaction with 2.25 g of tetrabutylammonium fluoride in 20 mL of dry THF. After stirring 45 min, the solution was poured into 50 mL of water. The water solution was extracted with ethyl acetate (3×75 mL). The combined organic solution was dried and evaporated leaving an oil which was purified by column chromatography on silica gel, eluting with 3% ethyl acetate in hexane. Residual t-butyldimethylsilanol was removed under reduced pressure at 45° C. This produced 1.00 g of the deprotected alkene; $^1H$ NMR ($CDCl_3$) δ 1.79–1.97 (m,12H), 2.65 (s,1H), 3.27 (s,1H), 3.59–4.59 (dt,2H, J=4, 14 Hz), 4.83 (s,1H), 5.837 (tt, 2H, J=4, 42 Hz), 6.77–6.80 (m,2H), 6.87–6.90 (dd,1H), 7.21–7.25 (m,1H).

(e) Synthesis of 4-(2,2-difluoroethoxy)-4-(3-hydroxyphenyl)spiro[1,2-dioxetane-3,2'-tricyclo[$3.3.1.1^{3,7}$] decane]. The alkene (30 mg) in 12 mL of $CH_2Cl_2$ was photooxygenated for 30 min at −78° C. using polymer-bound Rose Bengal. TLC showed complete consumption of the alkene and formation of a new material which emitted blue-green light when the plate was heated as well as dioxetane decomposition products. The sensitizer was filtered off, the solvent evaporated and the crude product chromatographed using 30% ethyl acetate in hexane. This yielded 24 mg of the dioxetane; $^1H$ NMR ($CDCl_3$) δ 1.04–2.12 (m,12H), 2.25 (s,1H), 3.05 (s,1H), 3.46–3.77 (m,2H), 5.46 (bs,1H), 5.84–6.24 (m,2H), 6.90–7.35 (m,4H). A repeat of the photooxygenation showed the alkene to be completely converted in under 10 min.

Example 8

Synthesis of Dioxetane 8

4-(2'-Fluoroethoxy)-4-(3-hydroxyphenyl)spiro[1,2-dioxetane-3,2'-tricyclo[$3.3.1.1^{3,7}$]decane].

(a) Synthesis of 2-fluoroethyl 3-hydroxybenzoate. A solution of 12.93 g of 3-hydroxybenzoic acid (93.7 mmol) in 11 mL of 2-fluoroethanol containing 3 drops of $H_2SO_4$ was refluxed for 16 hours. The cooled solution was evaporated and the white solid dissolved in ethyl acetate. The ethyl acetate was extracted with aqueous $NaHCO_3$ and $Na_2CO_3$ until neutral. The ethyl acetate solution was dried and evaporated under reduced pressure yielding 13.7 g of pale yellow oil which crystallized; $^1H$ NMR ($CDCl_3$) δ 4.50–4.83 (m,4H), 5.16 (s,1H), 7.05–7.09 (dd,1H), 7.31–7.37 (t,1H), 7.54–7.55 (t,1H), 7.65–7.68 (dd,1H).

(b) Synthesis of 2-fluoroethyl 3-t-butyldimethylsilyloxybenzoate. A solution of 2.73 g (1.1 eq.) of t-butyldimethylsilyl chloride and 1.24 g (1.1 eq.) of imidazole in 20 mL of DMF was stirred under argon for 15 min. The ester (3.04 g, 16.5 mmol) in 20 ML of DMF was added and the resulting solution stirred overnight. An additional 0.25 g of t-butyldimethylsilyl chloride and 0.11 g of imidazole were added and stirring continued for 30 min. The solution was extracted with hexane (7×100 mL) and the combined hexane solution was washed with water (3×100 mL). The hexane was dried and evaporated leaving 4.1 g of silylated ester; $^1H$ NMR ($CDCl_3$) δ 0.21 (s,6H), 1.00 (s,9H), 4.49–4.83 (m,4H), 7.04–7.07 (dd, 1H), 7.28–7.34 (t,1H), 7.52–7.53 (t,1H), 7.66–7.70 (dd,1H).

(c) Synthesis of [(3-t-butyldimethylsilyloxyphenyl)-(2-fluoroethoxy)methylene]tricyclo[$3.3.1.1^{3,7}$]decane. A three neck flask was purged with argon and charged with 60 mL of anhydrous THF. Titanium trichloride (8.38 g, 0.054 mol) was added with stirring and the flask was cooled in an ice bath. Lithium aluminum hydride (0.98 g, 0.027 mol) was added in small portions causing a brief exothermic reaction. After all of the LAH was added the cooling bath was removed and triethylamine (7.6 mL, 0.054 mol) was added. The black mixture was refluxed for 140 min under argon and then heating stopped. A solution of adamantanone (2.45 g, 16.3 mmol) and 2-fluoroethyl 3-t-butyldimethylsilyloxybenzoate (1.0 g, 3.35 mmol) in 20 mL of dry THF was added dropwise over 5 min. Reaction progress was monitored by TLC with 20% ethyl acetate in hexane. After 25 min, the mixture was diluted with hexane and decanted. The residue was washed several times using a total of ca. 450 mL of hexane. The combined hexane solution was filtered and evaporated leaving an oil which was purified by column chromatography on silica gel, eluting with 3% ethyl acetate in hexane yielding 1.68 g of alkene which contained some adamantylidene-adamantane; $^1$H NMR (CDCl$_3$) δ 0.20 (s,6H), 0.99 (s,9H), 1.66–1.98 (m,12H), 2.67 (s,1H), 3.31 (s,1H), 3.58–4.58 (m,4H), 6.75–6.82 (m,2H), 6.91–6.93 (dd,1H), 7.18–7.23 (t,1H).

(d) Synthesis of [(2-fluoroethoxy)-(3-hydroxyphenyl)-methylene]tricyclo[3.3.1.1$^{3,7}$]decane. The impure silyl-protected alkene (1.68 g) was deprotected by reaction with 1.27 g of tetrabutylammonium fluoride in 75 mL of dry THF. After stirring 1.5 hours, the solution was evaporated and the residue poured into 125 mL of water. The water solution was extracted with two 100 mL portions of ethyl acetate. The combined organic solution was dried and evaporated and the residue chromatographed using 1.5–10% ethyl acetate in hexane. Residual t-butyldimethylsilanol was removed under reduced pressure at 50° C. This produced 0.55 g of the deprotected alkene which crystallized; $^1$H NMR (CDCl$_3$) δ 1.79–1.99 (m,12H), 2.69 (s,1H), 3.31 (s,1H), 3.59–4.59 (m,4H), 4.78 (s,1H), 6.75–6.82 (m,2H), 6.89–6.92 (dd,1H), 7.19–7.24 (t,1H).

(e) Synthesis of 4-(2-fluoroethoxy)-4-(3-hydroxyphenyl) spiro[1,2-dioxetane-3,2'-tricyclo[3.3.1.1$^{3,7}$]decane]. The alkene (50 mg) in 20 mL of CH$_2$Cl$_2$ was photooxygenated for 40 min at −78° C. using polymer-bound Rose Bengal. TLC showed complete consumption of the alkene and formation of a new material which emitted blue-green light when the plate was heated. The sensitizer was filtered off and the solvent evaporated. The product was purified by preparative TLC with 20% ethyl acetate in hexane yielding 32 mg of the dioxetane; $^1$H NMR (CDCl$_3$) δ 1.03–1.09 (m,1H), 1.23–1.30 (m,1H), 1.45–1.90 (m,10H), 2.22 (S,1H), 3.09 (s,1H), 3.49–3.80 (m,2H), 4.45–4.82 (m,2H), 6.01 (bs,1H), 6.88–7.32 (m,4H).

Example 9

Synthesis of Dioxetane 9

4-(2'-Chloroethoxy)-4- (3-hydroxyphenyl)spiro[1,2-dioxetane-3,2'-tricyclo[3.3.1.1$^{3,7}$]decane].

(a) Synthesis of 2-chloroethyl 3-hydroxybenzoate. A solution of 14 g of 3-hydroxybenzoic acid (101 mmol) in 120 mL of 2-chloroethanol containing 1.5 mL of H$_2$SO$_4$ was refluxed for 4 hours. The cooled solution was diluted with water and extracted with ethyl acetate (2×200 mL). The ethyl acetate was extracted with aqueous NaHCO$_3$ and saturated NaCl. The ethyl acetate solution was dried and evaporated under reduced pressure yielding 20.92 g of product which contained a small amount of 2-chloroethanol; $^1$H NMR (CDCl$_3$) δ 3.805 (t,2H, J=5.4 Hz), 4.568 (t,2H, J=5.4 Hz), 6.26 (br s,1H), 7.09–7.12 (m,1H), 7.326 (t,1H, J=7.7 Hz), 7.58–7.65 (m,2H).

(b) Synthesis of 2-chloroethyl 3-t-butyldimethylsilyloxybenzoate. A solution of 23.58 g (156 mmol) of t-butyldimethylsilyl chloride and the ester from step (a) (20.92 g) in 85 mL of DMF was stirred under argon for 15 min. Imidazole (14.2 g, 208 mmol) was added and the resulting solution stirred overnight. The solution was poured into 200 mL of water and extracted with ether (5×100 mL). The combined ether solution was dried and evaporated leaving an orange oil. The silylated ester was purified by column chromatography using 3% ethyl acetate in hexane yielding 26.7 g of the product as a colorless oil which contained a small amount of t-butyldimethylsilanol; $^1$H NMR (CDCl$_3$) δ 0.223 (s,6H), 1.00 (s,9H), 3.805 (t,2H, J=5.7 Hz), 4.454 (t,2H, J=5.7 Hz), 7.03–7.07 (m,1H), 7.308 (t,1H, J=8 Hz), 7.52–7.54 (m,1H), 7.66–7.69 (m,1H).

(c) Synthesis of [(2-chloroethoxy)-(3-t-butyldimethylsilyloxyphenyl)methylene]tricyclo[3.3.1.1$^{3,7}$] decane. A three neck flask was purged with argon and charged with 150 mL of anhydrous THF. Titanium trichloride (55.4 g, 359 mmol) was added with stirring and the flask was cooled in an ice bath. Lithium aluminum hydride (6.82 g, 180 mmol) was added in small portions causing a brief exothermic reaction. The black mixture was diluted with 150 mL of dry THF. After all of the LAH was added, the cooling bath was removed and triethylamine (50.1 mL, 359 mmol) was added. The black mixture was refluxed for 2 hours under argon and then heating stopped. A solution of adamantanone (16.19 g, 108 mmol) and 2-chloroethyl 3-t-butyldimethylsilyloxybenzoate (11.31 g, 35.9 mmol) in 150 mL of dry THF was added dropwise over 1 hour. Reaction progress was monitored by TLC with 20% ethyl acetate in hexane. After 30 min, the mixture was cooled and left to stand under argon overnight. The mixture was diluted with 900 mL of hexane and filtered through filter paper. The residue was washed twice with 300 mL portions of hexane. The combined hexane solution was filtered and evaporated leaving an oil which was partially purified by column chromatography on silica gel, eluting with 5% ethyl acetate in hexane yielding 13.28 g of alkene which contained some adamantylideneadamantane; $^1$H NMR (CDCl$_3$) δ 0.204 (s,6H), 0.992 (s,9H), 1.67–1.98 (m,12H), 2.662 (br s,1H), 3.351 (br s,1H), 3.563 (t,4H, J=5.7 Hz), 3.675 (t,4H, J=5.7 Hz), 6.76–6.81 (m,2H), 6.90–6.93 (m,1H), 7.18–7.23 (t,1H).

(d) Synthesis of [(2-chloroethoxy)-(3-hydroxyphenyl) methylene]tricyclo[3.3.1.1$^{3,7}$]decane. The crude silyl-protected alkene (3.13 g) was deprotected by reaction with 2.42 g of tetrabutylammonium fluoride in 50 mL of dry THF. After stirring 15 min, the solution was evaporated and the residue poured into 70 mL of water. The water solution was extracted with three 100 mL portions of ethyl acetate. The combined organic solution was dried and evaporated and the residue chromatographed using 25% ethyl acetate in hexane. Residual t-butyldimethylsilanol was removed under reduced pressure. This produced 1.32 g of the deprotected alkene as an oil; $^1$H NMR (CDCl$_3$) δ 1.73–1.97 (m,12H), 2.67 (br s,1H), 3.343 (br s,1H), 3.567 (t,2H, J=5.4 Hz), 3.685 (t,2H, J=5.4 Hz), 5.298 (br s,1H), 6.75–6.89 (m,3H), 7.19–7.24 (t,1H).

(e) Synthesis of 4-(2-Chloroethoxy)-4-(3-hydroxyphenyl) spiro[1,2-dioxetane-3,2'-tricyclo[3.3.1.1$^{3,7}$]decane]. A small photooxygenation apparatus was charged with 61 mg (0.19 mmol) of the vinyl ether, 100 mg of polymer-bound Rose Bengal, and 8 mL of CH$_2$Cl$_2$ dried over MgSO$_4$. The resulting solution was then cooled to −78° C. with oxygen bubbling through it. After several minutes, the reaction solution was irradiated with a 1000 W sodium lamp for 30 min. TLC using 20% ethyl acetate in hexane showed conversion to a new material which emitted light when the plate was heated and decomposition product. The sensitizer was filtered off, the solvent evaporated and the material purified by chromatography on silica with 20% ethyl acetate in hexane which yielded 40 mg of dioxetane containing a small quantity of adamantanone: $^1$H NMR (CDCl$_3$) δ 1.07 (m, 1H), 1.26 (m, 1H), 1.42–2.16 (m, 10H), 2.205 (br s, 1H), 3.084 (br s, 1H), 3.48–3.60 (m, 1H), 3.64–3.84 (m, 3H), 5.643 (br s, 1H), 6.912 (dd, 1H), 6.98–7.44 (m, 3H).

Example 10

Synthesis of 1-(tri-n-octylphosphoniummethyl)-4-(tri-n-butylphosphoniummethyl)benzene dichloride, Enhancer A.

(a) A mixture of tri-n-butylphosphine (7 g, 34.6 mmol) in toluene (50 mL) was added dropwise to a mixture of α,α'-dichloro-p-xylene (12.1 g, 69.2 mmol, 2 eq.) in toluene (200 mL) under argon. The reaction mixture was stirred for 12 hours at room temperature under argon, after which time 4-(chloromethyl)benzyl-tri-n-butylphosphonium chloride had crystallized out of solution. The crystals were filtered and washed with toluene and hexane and air dried: $^1$H NMR (CDCl$_3$) δ 0.92 (t,9H), 1.44 (m, 12H), 2.39 (m, 6H), 4.35–4.40 (d, 2H), 4.56 (s, 2H), 7.36–7.39 (d, 2H), 7.47–7.51 (dd, 2H).

(b) To a mixture of 4-(chloromethyl)benzyl-tri-n-butylphosphonium chloride (3 g, 7.9 mmol) in DMF at room temperature, under argon was added tri-n-octylphosphine (4.39 g, 12 mmol). The reaction mixture was allowed to stir for several days, after which time TLC examination showed the reaction to be complete. The DMF was removed under reduced pressure, the residue washed with hexanes and toluene several times and then dried to give 1-(tri-n-octylphosphoniummethyl)-4-(tri-n-butylphosphoniummethyl)benzene dichloride as white crystals: $^1$H NMR (CDCl$_3$) δ 0.84 (t,9H), 0.89 (t, 9H), 1.22 (br s, 24H), 1.41 (m,24H), 2.34 (m, 12H), 4.35–4.40 (d, 4H), 7.58 (s, 4H); $^{13}$C NMR (CDCl$_3$) δ 13 δ 4, 13.94, 18.33, 18.62, 18.92, 19.21, 21.76, 21.81, 23.58, 23.64, 23.78, 23.98, 26.10, 26.65, 28.86, 30.68, 30.88, 31.53, 129.22, 131.22; $^{31}$P NMR (D$_2$O) δ 31.10. 31.94.

Example 11

Comparison of Chemiluminescence Intensities-Kinetic Profile

The improvement in detection speed afforded by compositions containing the phosphate dioxetane 5 is shown in Table 2 through a comparison with dioxetane 2 of the times to reach 95% of the maximum chemiluminescence intensities produced by reaction with AP. Three different reagent compositions containing either dioxetane 2, 4-methoxy-4-(3-phosphoryloxy-phenyl)spiro[1,2-dioxetane-3,2'-tricyclo-[3.3.1.1$^{3,7}$]decane], disodium salt, (LUMIGEN PPD, Lumigen, Inc.) or 5 were reacted at 37° C. with AP. Composition A consists of 0.33 mM dioxetane in 0.2M 2-methyl-2-amino-1-propanol buffer (pH 9.6) containing 1.0 mg/mL 1-(tri-n-octylphosphoniummethyl)-4-(tri-n-butylphosphonium-methyl) benzene dichloride (Enhancer A); 100 μL portions were reacted with 3.36×10$^{-16}$ mol of enzyme. Composition B consists of 0.33 mM dioxetane in 0.2M 2-methyl-2-amino-1-propanol buffer (pH 9.6) containing 0.5 mg/mL of polyvinylbenzyl-tributylphosphon ium chloride co-polyvinylbenzyltrioctyl-phosphonium chloride (containing a 3:1 ratio of tributyl:trioctyl groups) the preparation of which is described in European Patent Application 561,033 published Sep. 22, 1993 (Enhancer B); 100 μL portions were reacted with 3.36×10$^{-16}$ mol of enzyme. Composition C consists of 0.33 mM dioxetane in 0.2M 2-methyl-2-amino-1-propanol buffer (pH 9.6); 500 μL portions were reacted with 1.12×10$^{-15}$ mol of enzyme.

TABLE 2

Time to Reach 95% of Maximum Light Intensity from Alkaline Phosphatase-Triggering of Dioxetanes 2 and 5.

| Composition | 2 | 5 |
|---|---|---|
| A | 32 (min) | 6 |
| B | 37 | 4.3 |
| C | 6 | 4.5 |

Additionally, a higher plateau light intensity is acheived in Composition A with dioxetane 5 compared to dioxetane 2.

Example 12

Effect of the Concentration of Enhancer A on Chemiluminescence Intensity and Kinetics with Dioxetane 5

A concentration dependence study was conducted in an effort to find the optimum amount of enhancer A to use in the alkaline phosphatase-induced chemiluminescent reaction of dioxetane 5. Solutions of dioxetane 5 in 0.2M 2-methyl-2-amino-1-propanol buffer, pH 9.6 containing 0.88 mM Mg$^{+2}$ and 1, 0.5, 0.25 or 0.1 mg/mL of Enhancer A were prepared. Aliquots (100 μL) were equilibrated at 37° C. and reacted with 1.12×10$^{-17}$ moles of alkaline phosphatase. The plots of light intensity in Relative Light Units (RLU) vs. time shown in FIG. 1 unexpectedly show increasingly higher plateau light intensities and slower rise times as the amount of enhancer is reduced. A similar study with dioxetane 2 showed that the rise time to maximum light intensity decreased as the amount of enhancer is reduced but was an hour or more at all concentrations of enhancer from 0.1 mg/mL to 3 mg/mL.

Example 13

Effect of the Concentration of Enhancer B on Chemiluminescence Intensity and Kinetics with Dioxetane 5

Figure 2:
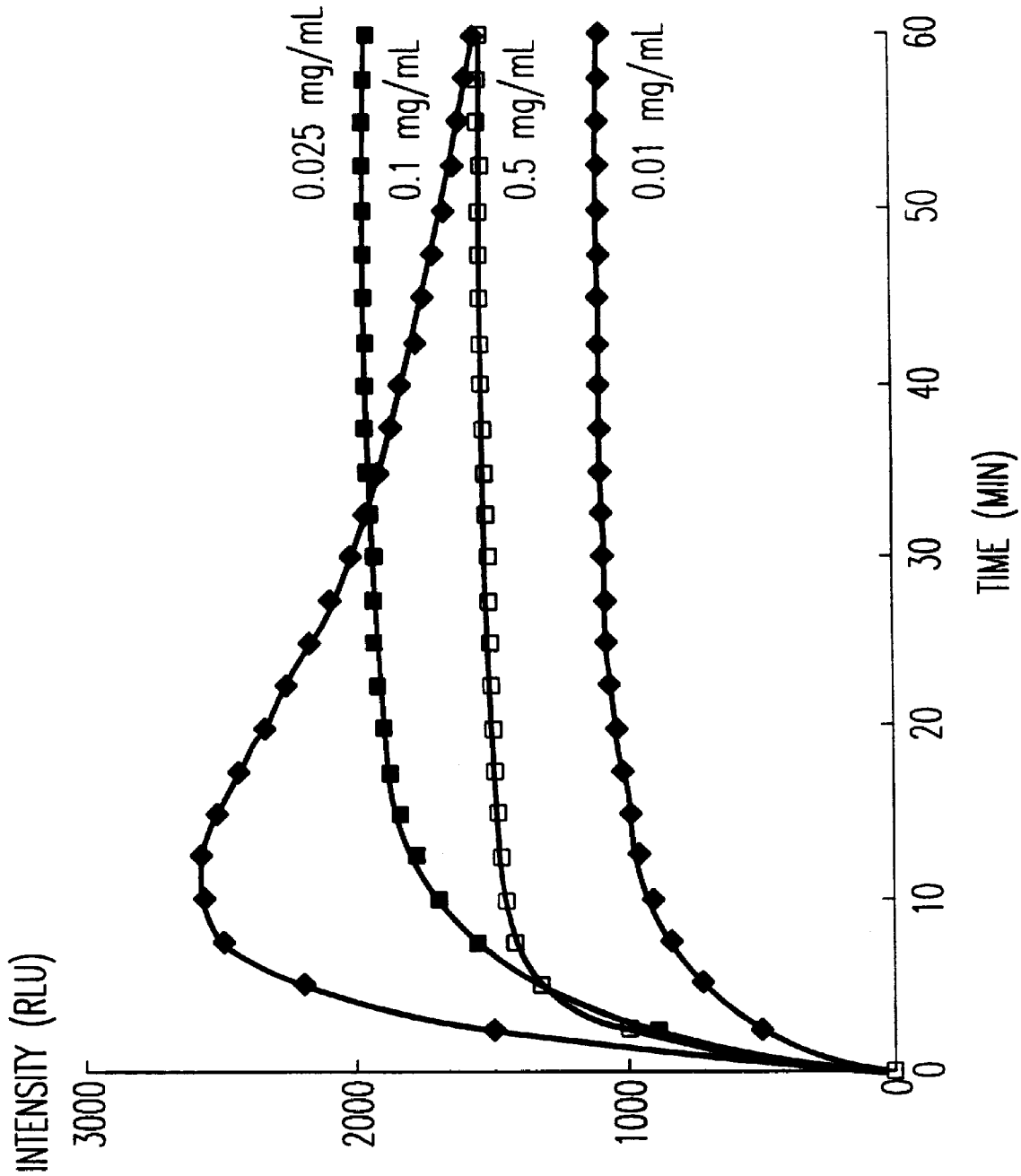

A concentration dependence study was conducted in an effort to find the optimum amount of Enhancer B to use in the alkaline phosphatase-induced chemiluminescent reaction of dioxetane 5. Solutions of dioxetane 5 in 0.2M 2-methyl-2-amino-1-propanol buffer, pH 9.6 containing 0.88 mM Mg$^{+2}$ and 0.5, 0.25, 0.1, 0.05 or 0.025 mg/mL of Enhancer B were prepared. Aliquots (100 μL) were equilibrated at 37° C. and reacted with 1.12×10$^{-17}$ moles of alkaline phosphatase. The plots of light intensity vs. time shown in FIG. 2 unexpectedly show slower rise times as the amount of enhancer is reduced from 0.5 to 0.01 mg/mL. A similar study with dioxetane 2 showed that the rise time to maximum light intensity was essentially constant at an hour or more as the amount of enhancer is reduced from 3 mg/mL to 0.1 mg/mL. The results shown in FIG. 2 show an unusual effect of the concentration of Enhancer B when used with dioxetane 5. The kinetics in terms of providing a flat plateau for the luminescence are well behaved at low concentration and at high concentration of the enhancer.

Example 14

Comparison of Chemiluminescence Intensity and Kinetics of Optimized Solutions Containing Dioxetane 2 or 5

Figure 3:
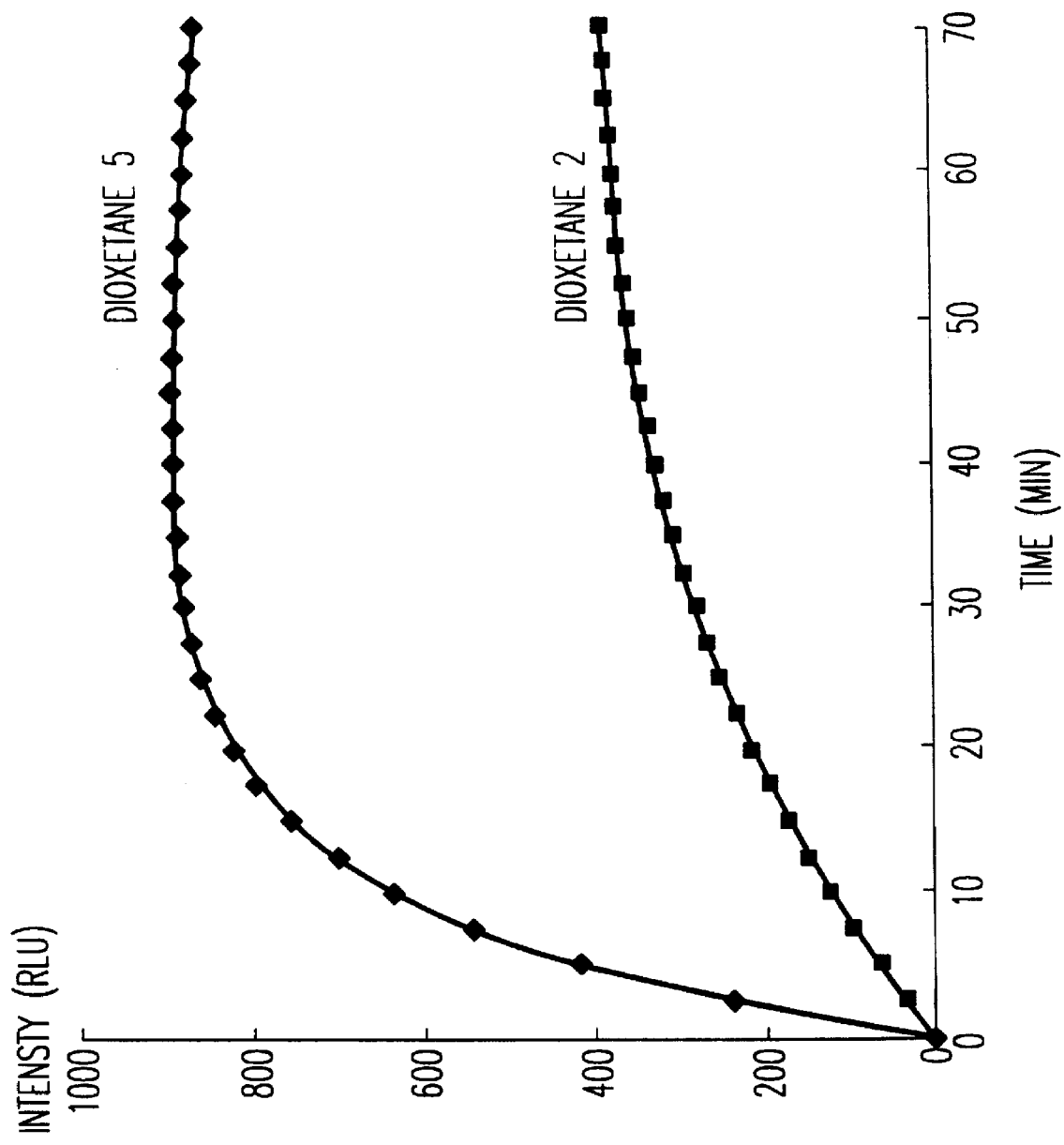
Figure 4:
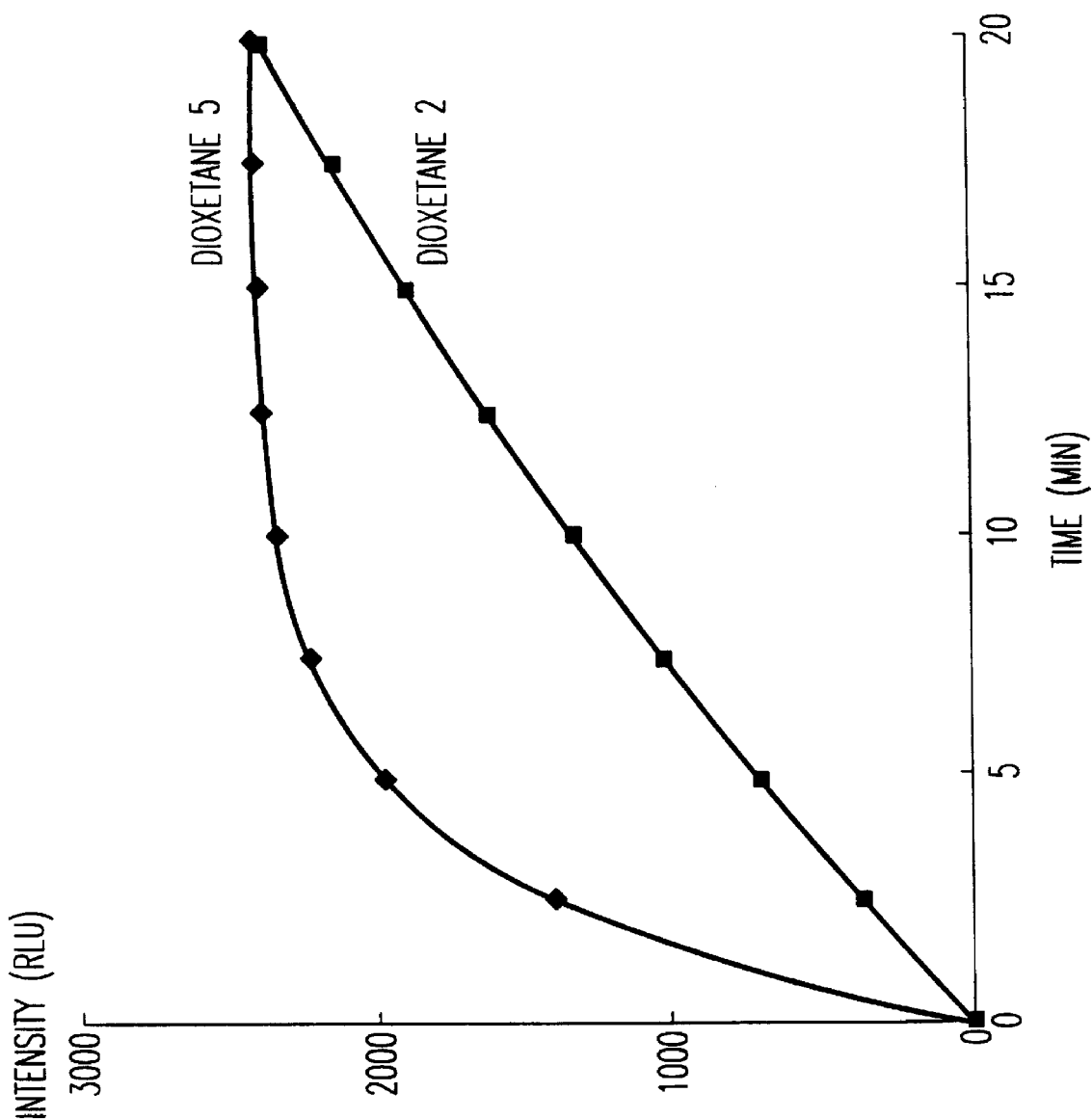

FIG. 3 illustrates the time profile and relative chemiluminescence intensities at 37° C. from two compositions, one containing 0.33 mM dioxetane 2 and 1 mg/mL of Enhancer A and the other containing 0.33 mM dioxetane 5 of the present invention and 0.1 mg/mL of Enhancer A. Light emission was initiated by addition of 1.12×10$^{-17}$ moles of AP to 100 μL of the dioxetane solution. The reagent containing dioxetane 5 of the present invention reaches a significantly higher maximum intensity and reaches a plateau much more rapidly. FIG. 4 illustrates the time profile and relative chemiluminescence intensities at 37° C. from two compositions, one containing 0.33 mM dioxetane 2 and 0.5 mg/mL of enhancer B and the other containing 0.33 mM dioxetane 5 of the present invention and 0.25 mg/mL of enhancer B. Light emission was initiated by addition of 1.12×10$^{-17}$ moles of AP to 100 μL of the dioxetane solution. The reagent containing dioxetane 5 of the present invention reaches a higher light intensity in the first 15 minutes which is advantageous in immunoassays.

Example 15

Linearity and Sensitivity of Detection of Alkaline Phosphatase with Dioxetane 5

Figure 5:
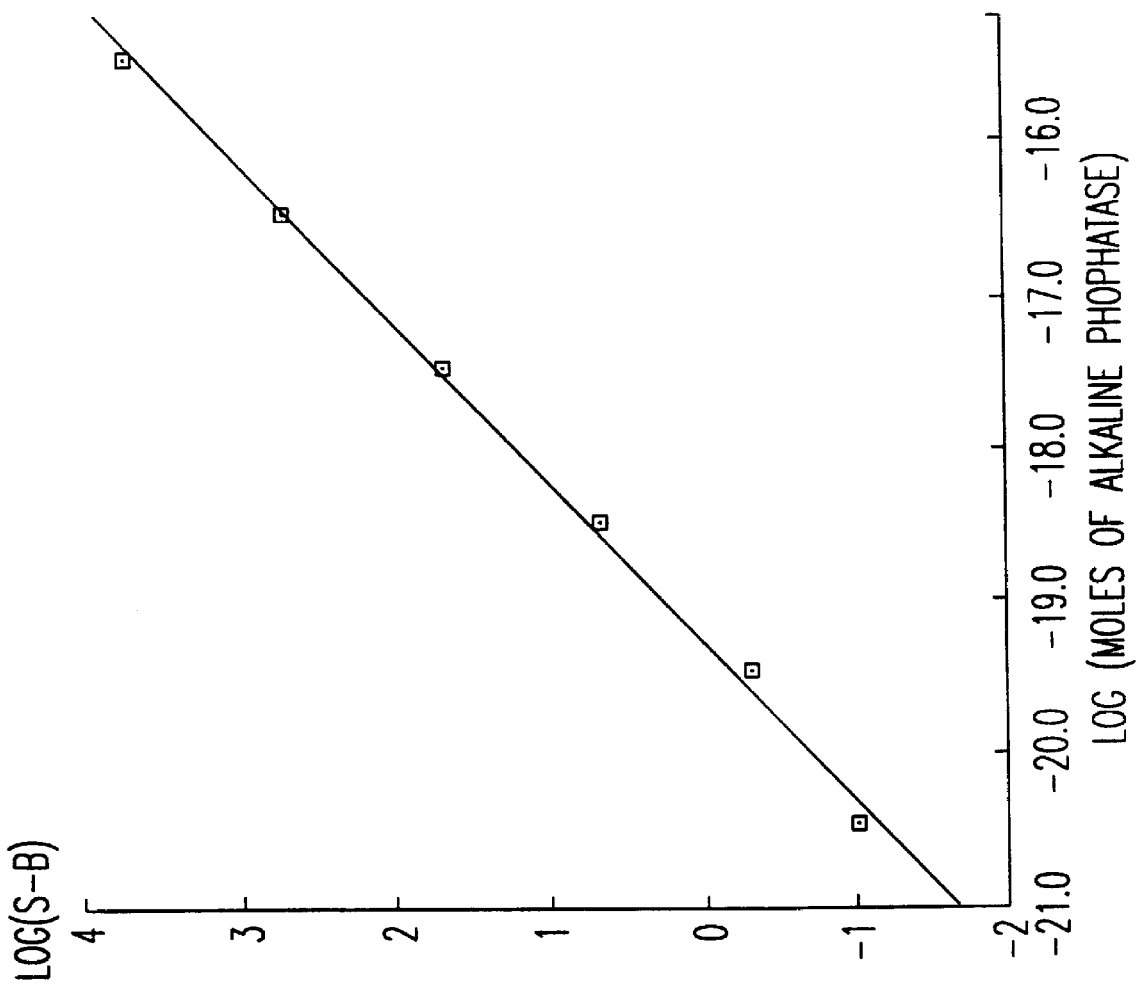

The linearity of detection of alkaline phosphatase using a reagent composition of the present invention containing dioxetane 5 was determined. To each of 48 wells in a 96-well microplate was added 50 μL of a 0.33 mM solution of dioxetane 5 in 0.2M 2-methyl-2-amino-1-propanol buffer, pH 9.6 containing 0.88 mM $Mg^{+2}$ and 1.0 mg/mL of Enhancer A. The plate was incubated at 37° C. and chemiluminescence emission initiated by addition of 3 μL of solutions of AP containing between $3.36 \times 10^{-16}$ mol and $3.36 \times 10^{-21}$ mol of enzyme. Light intensities were measured at 10 min. FIG. 5 shows the linear detection of alkaline phosphatase. The term S-B refers to the chemiluminescence signal (S) in RLU in the presence of AP corrected for background chemiluminescence (B) in the absence of AP. The calculated detection limit (twice the standard deviation of the background) was determined to be $1.25 \times 10^{-21}$ mol, or less than 1000 molecules of alkaline phosphatase under these conditions.

Example 16

Comparison of Rates of Base-Induced Decomposition of Hydroxy Dioxetanes

The first order decay of chemiluminescence of dioxetanes 1 and 3 in 0.2M 2-methyl-2-amino-1-propanol buffer, pH 9.6 containing 0.88 mM $Mg^{+2}$ and 1.0 mg/mL of Enhancer A at 37° C. was measured in a luminometer. The half-life of decay of chemiluminescence ($t_{1/2}$) of dioxetanes 1 and 3 in 0.2M 2-methyl-2-amino-1-propanol buffer, pH 9.6 containing 0.88 mM $Mg^{+2}$ and 1.0 mg/mL of Enhancer A correlate with the times required to reach the maximum light intensity ($I_{max}$) in the alkaline phosphatase-triggered decomposition of dioxetanes 2 and 5 in the same buffer solution. The half-life of decay of luminescence of the hydroxy dioxetane homologous to a phosphate-protected dioxetane, therefore, is useful for predicting the grow-in kinetics of light emission for phosphatase triggering of the corresponding phosphate dioxetane. In particular, hydroxy dioxetanes which show a faster $t_{1/2}$ than dioxetane 1 indicate that the corresponding phosphate dioxetanes are expected to reach $I_{max}$ more quickly. Other hydroxy dioxetanes (7–9) were then examined under the same conditions. Only the monochlorodioxetane (9) showed a slower half-life than dioxetane 1.

TABLE 3

Kinetics of Light Emission from Hydroxy Dioxetanes

| Dioxetane | $t_{1/2}$ (min) 37° C. |
|---|---|
| 1 | 15.9 |
| 3 | 2.0 |
| 7 | 2.8 |
| 8 | 6.1 |
| 9 | 17.1 |

Example 17

Comparison of Chemiluminescence Quantum Yields

The relative chemiluminescence quantum yields of dioxetanes 2 and 5 were determined in formulations containing 1 mg/mL or 0.1 mg/mL of Enhancer A in 0.2M 2-amino-2-methyl-1-propanol buffer, pH 9.6 containing 0.88 mM $Mg^{+2}$. A 100 μL aliquot of each reagent was completely dephosphorylated by addition of $3.36 \times 10^{-13}$ mol of alkaline phosphatase. The total amount of light emitted in Relative Light Units (RLU) was integrated until light emission ceased. A similar comparison was also made with 500 μL portions of formulations without any enhancer using 0.75M 2-amino-2-methyl-1-propanol buffer, pH 9.6 containing 0.88 mM $Mg^{+2}$. Dioxetane 5 produces more light than dioxetane 2.

TABLE 4

Total Light Intensity from Phosphate Dioxetanes

|  | Dioxetane 2 | Dioxetane 5 |
|---|---|---|
| No enhancer | $4.41 \times 10^4$ RLU | $9.65 \times 10^4$ |
| Enhancer A |  |  |
| (1 mg/mL) | $9.24 \times 10^6$ | $1.23 \times 10^7$ |
| (0.1 mg/mL) |  | $1.01 \times 10^7$ |

Example 18

Fluoride Induced Chemiluminescence of Haloalkoxy Dioxetanes

A portion of each of the purified dioxetanes 3 and 6–9 was separately mixed with a solution of 0.1M tetrabutylammonium fluoride in DMSO causing a brief flash of blue-green light which could be seen in a darkened room by eye. Chemiluminescence persisted for a few minutes. Light emission produced in this manner could also be produced with the dioxetane deposited on a silica gel TLC plate.

Example 19

Chemiluminescent Detection of Alkaline Phosphatase on Membrane

The advantage of a composition of the present invention for the chemiluminescent detection of enzymes on the surface of blotting membranes is demonstrated in the following example. Solutions of alkaline phosphatase in water containing from 1.1 fmol to 1.1 amol were applied to identical nylon membranes (Micron Separations Inc., Westboro, Mass.). The membranes were air dried for 5 min and soaked briefly with a reagent containing 1 mg/mL of Enhancer A in 0.2M 2-amino-2-methyl-1-propanol buffer, pH 9.6 containing 0.88 mM MgCl and either 0.33 mM dioxetane 2 or dioxetane 5. The membranes were placed between transparent plastic sheets and exposed to x-ray film (Kodak X-OMAT AR, Rochester, N.Y.). FIG. 6 shows that in a comparison of the two reagents the light produced using dioxetane 5 led to more intense images and better detection sensitivity. These results illustrate the improved performance of dioxetane 5 which is to be expected in Western blotting, Southern blotting, DNA fingerprinting and other blotting applications.

We claim:

1. A dioxetane of the formula

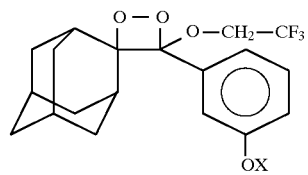

wherein X is a group which is removable by admixture of said dioxetane with an enzyme specific for said group X in an aqueous composition or X is H.

2. The dioxetane of claim 1, wherein X is selected from the group consisting of $OPO_3^{2-}$ salt, $OSO_3^-$ salt, β-D-galactosidoxy and β-D-glucuronidyloxy groups.

3. A compound having the formula:

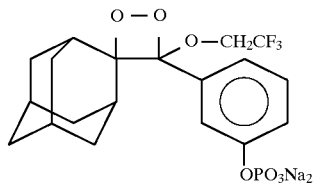

4. A composition for producing light comprising in an aqueous solution;

(a) a dioxetane of claim 1, 2 or 3, and (b) an enhancer substance which increases the quantity of light produced by reacting the dioxetane with the reagent compared to the amount which is produced in the absence of the enhancer.

5. The composition of claim 4 wherein the enhancer is selected from the group consisting of polymeric quaternary ammonium salt surfactants, polyvinylbenzyltrialkylphosphonium group-containing polymers and dicationic surfactants of the formula:

wherein each of A is independently selected from P and N atoms and wherein Link is an organic linking group containing at least two carbon atoms selected from the group consisting of substituted and unsubstituted aryl, alkyl, alkenyl and alkynyl groups and wherein Link may contain heteroatoms and wherein R is selected from lower alkyl or aralkyl containing 1 to 20 carbon atoms and wherein Y is a halide anion.

* * * * *